(12) United States Patent
McClelland

(10) Patent No.: US 9,573,128 B1
(45) Date of Patent: Feb. 21, 2017

(54) FLUIDICS DEVICE ALLOWING FLUID FLOW BETWEEN A PLURALITY OF WELLS

(71) Applicant: SciKon Innovation, Inc., Research Triangle Park, NC (US)

(72) Inventor: Randall McClelland, Chapel Hill, NC (US)

(73) Assignee: SciKon Innovation, Inc., Research Triangle Park, NC (US)

( * ) Notice: Subject to any disclaimer, the term of this patent is extended or adjusted under 35 U.S.C. 154(b) by 541 days.

(21) Appl. No.: 14/016,913

(22) Filed: Sep. 3, 2013

Related U.S. Application Data

(60) Provisional application No. 61/697,395, filed on Sep. 6, 2012.

(51) Int. Cl.
*B01L 3/00* (2006.01)
*C12M 1/26* (2006.01)
*C12M 1/12* (2006.01)
*C12M 1/32* (2006.01)

(52) U.S. Cl.
CPC ......... *B01L 3/502715* (2013.01); *C12M 23/12* (2013.01); *C12M 25/04* (2013.01); *B01L 3/5085* (2013.01)

(58) Field of Classification Search
CPC ................................................ B01L 3/502715
USPC ...................................................... 435/309.1
See application file for complete search history.

(56) References Cited

U.S. PATENT DOCUMENTS

| D246,466 | S | 11/1977 | Attree et al. |
| 4,239,853 | A * | 12/1980 | Bradley ................. C12M 23/12 |
| | | | 422/561 |
| D264,810 | S | 6/1982 | Voltmann |
| D271,239 | S | 11/1983 | Lemieux et al. |
| 4,483,925 | A * | 11/1984 | Noack .................... B01L 3/5085 |
| | | | 141/110 |
| D284,699 | S | 7/1986 | Jolley |
| D288,484 | S | 2/1987 | Mitchell |
| D302,207 | S | 7/1989 | Matkovich |
| D303,149 | S | 8/1989 | Andersen |
| 5,130,105 | A | 7/1992 | Carter et al. |
| D335,348 | S | 5/1993 | Frenkel et al. |

(Continued)

FOREIGN PATENT DOCUMENTS

GB          2147100 A   *  5/1985   ............ B01L 3/0203
WO     WO2011/137039    * 11/2011

OTHER PUBLICATIONS

Inamdar NK.; Borenstein JT.; Microfluidic cell culture models for tissue engineering, Current Opinion in Biotechnology, 2011, 22, 1-9.

(Continued)

*Primary Examiner* — Michael Hobbs
(74) *Attorney, Agent, or Firm* — NK Patent Law, PLLC

(57) ABSTRACT

Disclosed are fluidics devices and assemblies allowing for fluid flow between a plurality of wells. The fluidics devices and assemblies that are provided mimic in vivo tissue environments by allowing for initially segregated tissue cultures that can then be linked through fluid flow to measure integrated tissue response. The devices and assemblies provide a pumpless system using surface tension, gravity, and channel geometries. By linking human tissue functional systems to better simulate in vivo feedback and response signals between the tissues, the need for testing in animals can be minimized.

33 Claims, 8 Drawing Sheets

(56) References Cited

U.S. PATENT DOCUMENTS

| | | | |
|---|---|---|---|
| 5,417,923 A | 5/1995 | Bojanic et al. | |
| 5,487,872 A | 1/1996 | Hafeman et al. | |
| 5,588,441 A | 12/1996 | Fishman | |
| 5,801,055 A | 9/1998 | Henderson | |
| 5,817,510 A | 10/1998 | Pandey et al. | |
| D404,497 S | 1/1999 | Lahm et al. | |
| D411,308 S | 6/1999 | Pandey et al. | |
| 5,993,745 A | 11/1999 | Laska | |
| D420,743 S | 2/2000 | Monks | |
| 6,019,225 A | 2/2000 | Kalmakis et al. | |
| 6,106,783 A | 8/2000 | Gamble | |
| 6,395,234 B1 | 5/2002 | Hunnell et al. | |
| 6,439,884 B1 | 8/2002 | Cronin | |
| 6,485,690 B1* | 11/2002 | Pfost | B01J 19/0046 422/552 |
| D469,544 S | 1/2003 | Lafond et al. | |
| 6,632,656 B1* | 10/2003 | Thomas | B01L 3/5027 435/288.5 |
| 6,637,463 B1* | 10/2003 | Lei | B01F 5/0403 137/803 |
| 6,875,405 B1 | 4/2005 | Mathus et al. | |
| 6,939,709 B2* | 9/2005 | Henderson | B01L 3/50255 422/520 |
| 6,987,253 B2* | 1/2006 | Bedingham | B01L 3/5025 219/752 |
| 7,005,029 B2 | 2/2006 | Khan et al. | |
| 7,279,134 B2* | 10/2007 | Chan | B01D 61/022 216/2 |
| D574,505 S | 8/2008 | Muller-Cohn et al. | |
| 7,452,510 B2* | 11/2008 | Weinfield | B01D 61/18 141/130 |
| 7,560,073 B1* | 7/2009 | Peters | B01L 3/502723 422/646 |
| D632,803 S | 2/2011 | Motadel et al. | |
| 7,922,672 B2 | 4/2011 | Hein, Jr. et al. | |
| D672,053 S | 12/2012 | Chen et al. | |
| 8,377,685 B2 | 2/2013 | Meyvantsson | |
| D699,370 S | 2/2014 | Motadel et al. | |
| D699,859 S | 2/2014 | Motadel | |
| D720,468 S | 12/2014 | Calderwood et al. | |
| D724,236 S | 3/2015 | Motadel et al. | |
| D730,537 S | 5/2015 | Burroughs et al. | |
| 2003/0138941 A1* | 7/2003 | Gong | B01L 3/5027 435/287.2 |
| 2004/0101439 A1* | 5/2004 | Fusco | B01J 19/0046 506/33 |
| 2005/0072030 A1 | 4/2005 | Wu | |
| 2005/0147958 A1* | 7/2005 | Hassanein | A01N 1/02 435/1.1 |
| 2006/0093530 A1 | 5/2006 | Ueda | |
| 2006/0137434 A1* | 6/2006 | Cohen | B01L 3/502746 435/287.1 |
| 2007/0166816 A1 | 7/2007 | Campbell et al. | |
| 2008/0060424 A1* | 3/2008 | Babic | B01L 3/5023 73/61.41 |
| 2009/0023610 A1* | 1/2009 | Peytavi | B01L 3/5027 506/39 |
| 2010/0041143 A1* | 2/2010 | Nishiyama | C12M 23/10 435/375 |
| 2010/0233694 A1* | 9/2010 | Kopf-Sill | G01N 33/5091 435/6.14 |
| 2010/0284859 A1* | 11/2010 | Cooney | B01J 19/0046 422/68.1 |
| 2011/0236278 A1 | 9/2011 | Motadel et al. | |
| 2012/0135452 A1 | 5/2012 | Shuler et al. | |
| 2012/0328488 A1 | 12/2012 | Puntambekar | |

OTHER PUBLICATIONS

Domanksy K.; Inman W.; Serdy J.; Dash A.; Lim M.; Griffith L.; Perfused multiwell plate for 3D liver tissue engineering, Lab Chip, 2010, 10, 51-58.

Dance A, Enter the Third Dimension, Cell culture goes 3-D with devices that better mimic in vivo conditions, The Scientist, Sep. 1, 2012.

Keenan T & Folch A, Biomolecular gradients in cell culture systems, Lab Chip, 2008, 8, 34-57.

USPTO, Notice of Allowance for Design U.S. Appl. No. 29/465,155, mailed on May 4, 2016.

ISA/KR, International Search Report and Written Opinion for PCT Patent Application No. PCT/US2016/023844, mailed on Jul. 25, 2016.

Toh, Yi-Chin et al., "A microfluidic 3D hepatocyte chip for drug toxicity testing", Lab on a Chip, 2009, vol. 9, No. 14, pp. 2026-2035.

Ye, Nannan et al., "Cell-based high content screening using an integrated microfluidic device", Lab on a Chip, 2007, vol. 7, No. 12, pp. 1696-1704.

Kim, Jeongyun et al., "A programmable microfluidic cell array for combinatorial drug screening", Lab on a Chip, 2012, vol. 12, No. 10, pp. 1813-1822.

* cited by examiner

FLUIDICS DEVICE ALLOWING FLUID FLOW BETWEEN A PLURALITY OF WELLS

CROSS REFERENCE TO RELATED APPLICATION

This application claims priority to U.S. Provisional Patent Application No. 61/697,395 filed Sep. 6, 2012, the disclosure of which is incorporated herein by reference in its entirety.

TECHNICAL FIELD

This disclosure is related to a fluidics device for allowing fluid flow between a plurality of wells.

BACKGROUND

It is estimated to cost on the order of $1 B dollars to bring a drug candidate to market and the pharmaceutical industry is enhancing its chances of success by investing in human pre-clinical research. This money has driven the absorption, distribution, metabolism, elimination, and toxicology (AD-MET) market in human-based products to a $5 billion dollar annual industry. The current technology for testing drug candidates is based on homogeneous culture techniques and animal models. Thus, there is an unmet need for biotool devices capable of linking human tissue functional systems to better simulate in vivo feedback and response signals between tissues and to minimize testing in animals.

Accordingly, such biotool devices and assemblies are provided in the present disclosure.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein is a fluidics device for allowing fluid flow between a plurality of wells. The fluidics device includes a dosing well positioned upstream from a plurality of wells for containing a respective host fluid and one or more channels extending between adjacent upstream and downstream wells to define a channel fluid flow path there between, such that a dosing fluid deposited into the dosing well flows to the respective host fluid of the adjacent downstream well along the channel fluid flow path there between, and the respective host fluid subsequently flows to each adjacent downstream well along the channel fluid flow path there between.

According to one or more embodiments, the fluidics device can include a wick downstream from at least a portion of the plurality of wells. The wick is in fluid contact with the channel fluid flow path for regulating fluid flow through the plurality of wells.

According to one or more embodiments, the fluidics device can include a collection well downstream from the plurality of wells to collect the respective host fluid after having flowed through the plurality of wells. The collection well of the fluidics device can define an aperture, wherein the aperture is defined at a lower portion of a floor of the collection well.

According to one or more embodiments, the wick can be contained in the collection well such that the wick is in fluid contact with the channel fluid flow path for regulating fluid flow through the plurality of wells.

According to one or more embodiments, the surface of one or more of the plurality of wells of the fluidics device can be modified with one or both of a chemical layer or a protein layer to support a cell culture. The protein layer for supporting the cell cultures can include one or more of collagen I, collagen II, collagen III, laminin, or fibronection, or combinations thereof.

Disclosed herein is an assembly for allowing fluid flow between a plurality of wells. The assembly includes one or more fluidics devices nestably engaged and one or more reservoir trays nestably engaged on top of the fluidics device(s). The reservoir tray includes at least one chamber for containing a respective chamber fluid and an aperture defined in the chamber floor and configured such that the aperture is positioned above a dosing well of the fluidics device when in nesting engagement with the fluidics device. The floor of the chamber is angled and the aperture is defined at a lower portion of the chamber floor such that the chamber fluid flows through the aperture into the dosing well when the reservoir tray and the fluidics device are nestably engaged.

According to one or more embodiments, the assembly can include one or more reservoir trays nestably engaged underneath the fluidics device(s). The fluidics device can include a collection well downstream from the plurality of wells and the collection well defines an aperture such that fluid from the collection well flows through the aperture into the chamber of the reservoir tray nestably engaged underneath the fluidics device(s).

According to one or more embodiments, the assembly can further include a cover tray configured for nesting engagement on top of the reservoir tray nestably engaged on top of the fluidics device.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

The presently disclosed subject matter provides fluidics devices and assemblies that in one aspect are capable of linking human functional systems to better simulate in vivo feedback and response signals between tissues and to minimize the need for testing in animal models. For example, the devices and assemblies of the presently disclosed subject matter can mimic in vivo tissue environments by allowing for initially segregated tissue cultures that can then be linked through fluid flow to measure integrated tissue response. The devices and assemblies of the present disclosure can allow for cell culture integration and media flow activated on demand. The devices and assemblies of the presently disclosed subject matter can provide a pumpless system using surface tension, gravity, and channel geometries. The devices and assemblies of the present disclosure can provide timed and tempered nutrient flow through integrated channels. The devices and assemblies of the present disclosure can provide an option to induce toxin exposure (e.g., drug exposure) at a particular cell site.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

Figure 1:
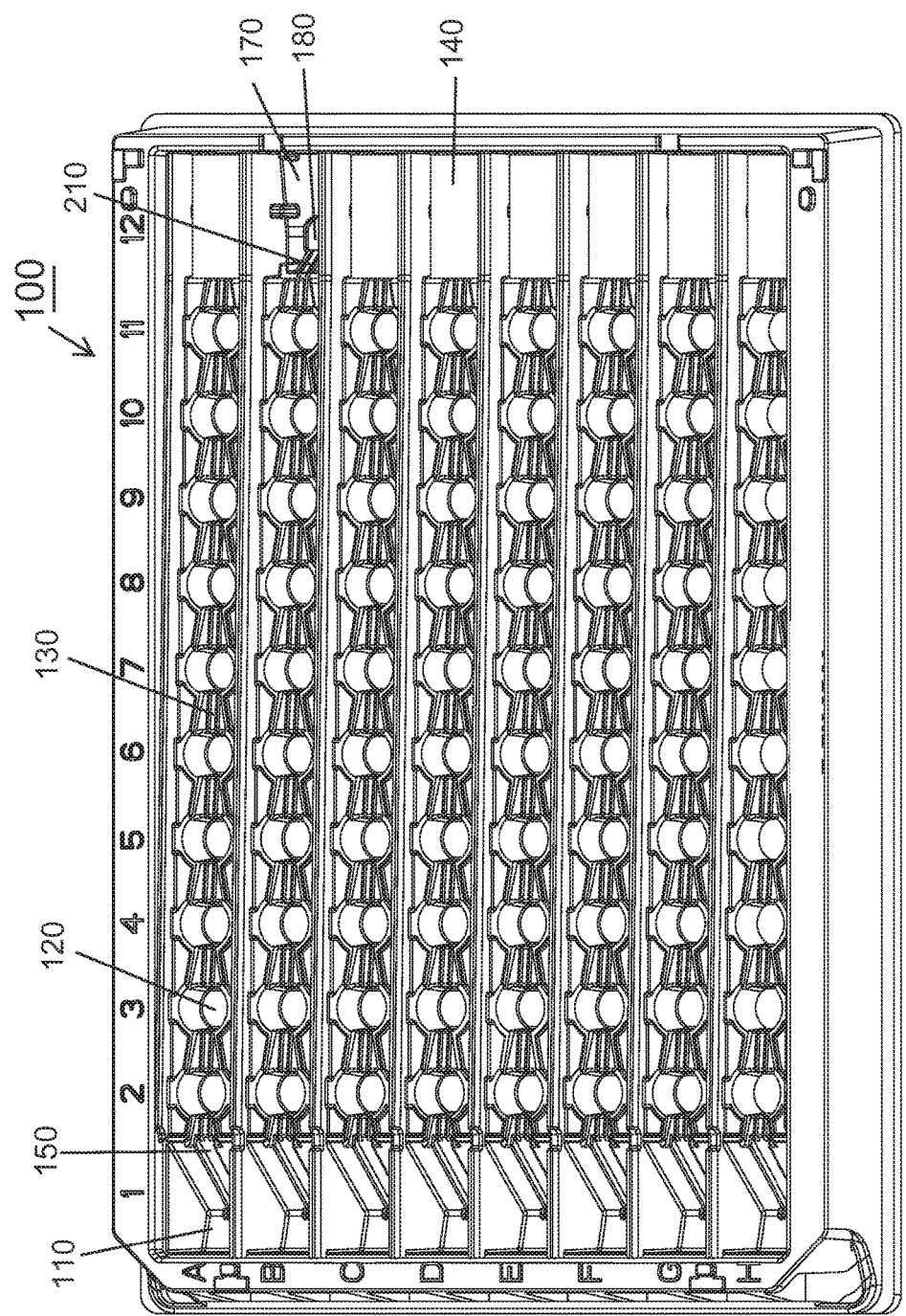
FIG. 1 is a perspective view of a fluidics device in accordance with embodiments of the present disclosure.

FIG. 1 is a perspective view of a fluidics device 100 in accordance with embodiments of the present disclosure. The fluidics device 100 can include a dosing well 110 positioned upstream from a plurality of wells 120 for containing a respective host fluid, and one or more channels 130 extending between adjacent upstream and downstream wells 120 to define a channel fluid flow path 130 there between such that a dosing fluid deposited into the dosing well 110 flows to the respective host fluid of the adjacent downstream well 120 along the channel fluid flow path 130 there between, and the respective host fluid subsequently flows to each adjacent downstream well 120 along the channel fluid flow path 130 there between.

According to one or more embodiments, the fluidics device 100 can have a structure such that each adjacent downstream well 120 is oriented in a step-down position relative to its adjacent upstream well 120. An example of a fluidics device 100 having this step-down well positioning structure is shown in FIG. 1.

According to one or more embodiments, the fluidics device 100 can include a wick 140 downstream from at least a portion of the plurality of wells 120. The wick 140 is in fluid contact with the channel fluid flow path 130 for regulating fluid flow through the plurality of wells 120. For purposes of the specification and claims, the term "wick" is meant to be used in the broadest sense to refer to a piece of material that can convey liquid by capillary action.

According to one or more embodiments, the fluidics device 100 can include a dosing well channel 150 extending from a bottom of the dosing well 110 to the channel fluid flow path 130 such that the dosing fluid flows to the respective host fluid of the adjacent downstream well 120 through the dosing well channel 150 and along the channel fluid flow path 130. A side of the dosing well 110 can define an angle of greater than 90° extending from a bottom of the dosing well 110 up to the channel fluid flow path 130 of the adjacent well 120. According to one or more embodiments, the fluidics device 100 can include a collection well 170 downstream from the plurality of wells 120 to collect the respective host fluid after having flowed through the plurality of wells 120. The collection well 170 of the fluidics device 100 can include a floor that defines a divot 180, wherein the floor is angled such that the divot 180 is defined at a lower portion of the floor. In certain embodiments according to the present disclosure as described herein below, the lower portion of the floor of the collection well 170 can define an aperture as an alternative to the divot 180. In another example, the divot 180 can be converted to an aperture for use of the fluidics device 100 in an assembly as described herein below.

In accordance with embodiments of the present disclosure, the collection well 170 of fluidics device 100 can include one or more collection well channels 210 extending from the channel fluid flow path 130 to a bottom of the collection well 170 such that the respective host fluid of the adjacent upstream well 120 flows along the channel fluid flow path 130 and through the collection well channel 210 into the collection well 170. The collection well channel 210 can have a width ranging from about 10 to 3500 microns and a depth ranging from about 10 to 3500 microns. The collection well 170 can define a ramp extending from a bottom of the collection well 170 up to the channel fluid flow path 130 of the adjacent upstream well 120. The ramp can include 1, 2, 3, or 4 of the collection well channels 210 that are contiguous with the ramp.

Figure 2:
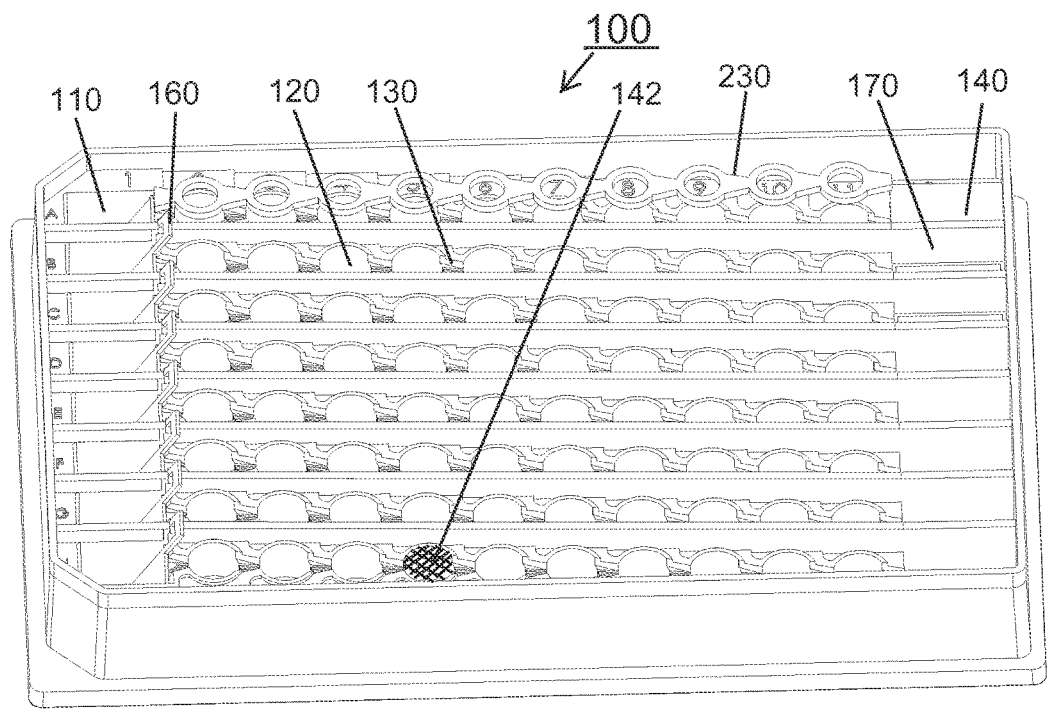
FIG. 2 is a perspective view of the fluidics device of FIG. 1 illustrating dosing well channel cover to enclose dosing well channel and channel cover to enclose the one or more channels extending between the adjacent wells in accordance with embodiments of the present disclosure.

FIG. 2 is a perspective view of the fluidics device 100 in accordance with embodiments of the present disclosure. FIG. 2 illustrates that the fluidics device 100 can include a dosing well channel cover 160 configured to enclose the dosing well channel 150. An example of the dosing well channel cover 160 is shown in FIG. 2 where each of the 8 dosing wells (A-H) are covered with the dosing well channel cover 160. FIG. 2 also illustrates that the fluidics device 100 can include a channel cover 230 configured for engagement on top of the one or more channels 130 extending between the adjacent wells 120 to enclose the channels 130.

The wick of the present disclosure can define any shape that is suitable for being in fluid contact with the channel fluid flow path 130 and for regulating fluid flow through the plurality of wells 120. For example, the wick of the presently disclosed subject matter can be any absorbent material. The wick can regulate fluid flow through the plurality of wells 120 at a rate ranging from 0.0007 ml/min to 30 ml/min. In one example, the respective host fluid after having flowed through each of the plurality of wells 120 and onto the wick can evaporate off the wick.

Figures 3A, 3B, 3C:
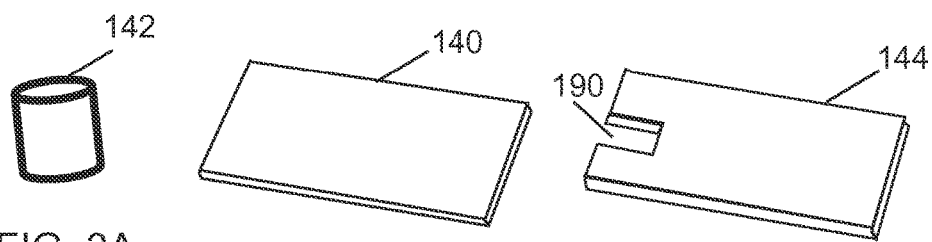
FIGS. 3A-3C illustrate the wick separate from the fluidics device of FIG. 2 in accordance with embodiments of the present disclosure.

FIG. 2 illustrates two examples of the wick (i.e wick 140 and wick 142) at separate positions downstream from a portion of the plurality of wells 120. FIGS. 3A-3C illustrate the wick in accordance with one or more embodiments of the present disclosure. FIG. 3A illustrates an example of the wick 142 having a cylindrical shape. FIG. 3C illustrates an example of the wick 140 defining a generally flat shape. The wick defining a generally flat shape can define a gap such that only a portion of an edge of the wick is in fluid contact with the channel fluid flow path 130. FIG. 3C illustrates an example of the wick 144 defining a gap 190.

The wick 142 defining a cylindrical shape is illustrated in FIG. 2 and FIG. 3A. The wick of the present disclosure can be positioned anywhere downstream from at least a portion of the plurality of wells 120. For example, the wick 142 defining a cylindrical shape is shown contained in well 120 in row eight of the fluidics device 100 in FIG. 2 such that the wick 142 is in fluid contact with the channel fluid flow path 130 for regulating fluid flow through the plurality of upstream wells 120.

The wick can define a generally flat shape. According to one or more embodiments, the wick 140 or 144 defining a generally flat shape can be contained in the collection well 170 such that the wick 140 or 144 is in fluid contact with the channel fluid flow path 130 for regulating fluid flow through the plurality of wells 120. The wick defining a generally flat shape can be carried by a shoulder defined by the collection well 170 such that the wick does not contact a bottom surface of the collection well 170. An example of the wick 140 defining a generally flat shape and carried by a shoulder defined by the collection well 170 is illustrated in FIG. 2 and in FIG. 3B. The wick defining a generally flat shape can be carried by one or more posts defined by the collection well 170 such that the wick does not contact a bottom surface of the collection well 170. In one embodiment, the wick can define a generally flat shape and can be carried by six of the posts defined by the collection well 170 such that the wick does not contact a bottom surface of the collection well 170.

Figure 4:
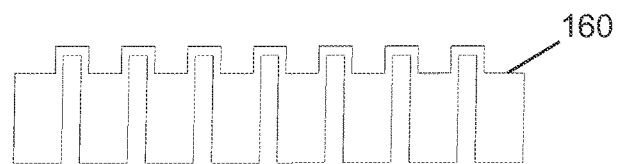
FIG. 4 illustrates the dosing well channel cover separate from the fluidics device of FIG. 2 in accordance with embodiments of the present disclosure.

FIG. 4 illustrates the dosing well channel cover 160 separate from the fluidics device 100.

Figure 5:
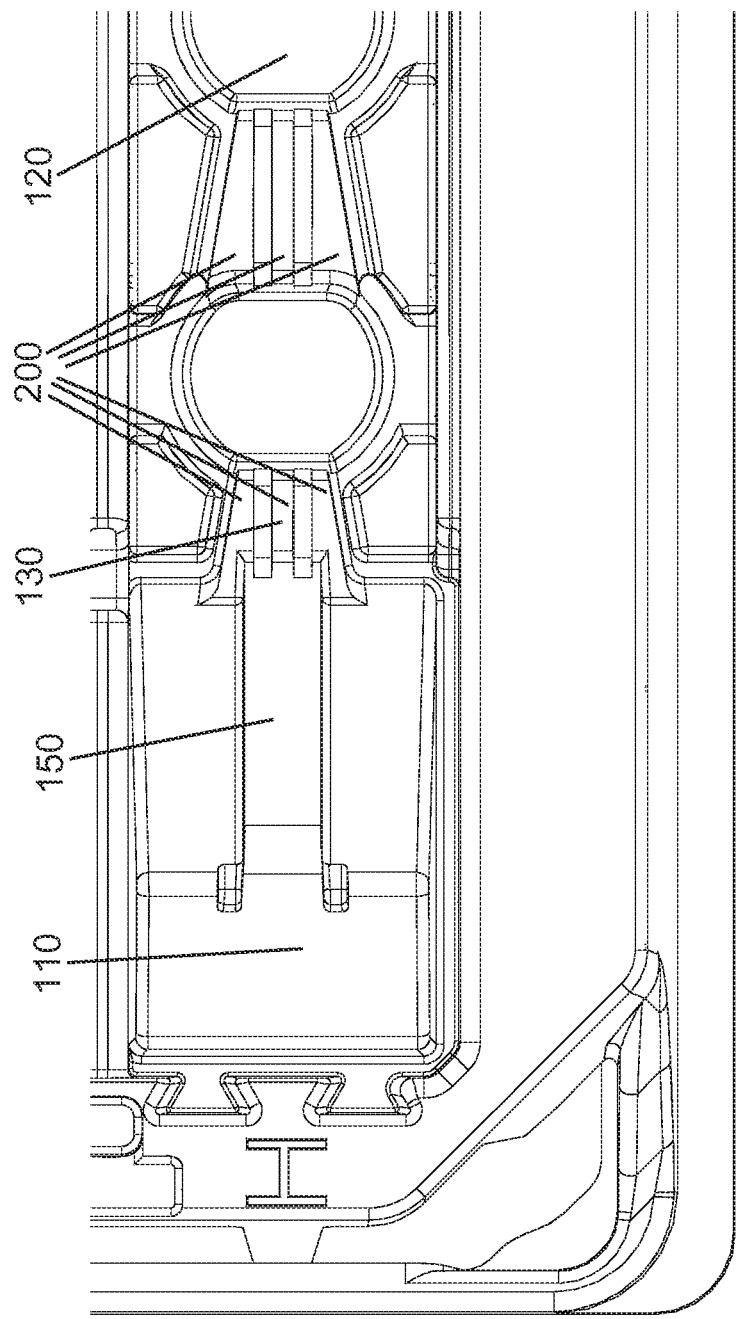
FIG. 5 illustrates an enlarged top view of the fluidics device of FIG. 1 showing an enlarged view of the dosing well, dosing well channel, adjacent downstream well, and the one or more channels extending there between in accordance with embodiments of the present disclosure.

FIG. 5 illustrates a top view of the fluidics device of FIG. 1 showing an enlarged view of the dosing well 110, dosing well channel 150, adjacent downstream well 120, and the one or more channels 130 extending there between in accordance with embodiments of the present disclosure. The dosing well channel 150 can have a width ranging from about 10 to 3500 microns and a depth ranging from about 10 to 3500 microns. The dosing well channel 150 can include 2, 3, or 4 channels contiguous with the dosing well channel 150 and each of the channels can have a width ranging from about 200 to 1500 microns and a depth ranging from about 10 to 1500 microns.

The one or more channels 130 extending between adjacent upstream and downstream wells 120 of the fluidics device 100 can have a width ranging from 10 to 3500 microns and a depth of 10 to 1500 microns. An example of a fluidics device 100 having a single channel 130 is shown in FIG. 5. The channel 130 can define a triangular-shape that extends between each of the adjacent wells 120. The triangular-shape channel 130 can be positioned such that the triangular shape generally converges at each adjacent downstream well 120. An example of a fluidics device 100 having the triangular-shape channel 130 positioned such that the triangular shape generally converges at each adjacent downstream well 120 is shown in FIG. 5.

The fluidics device 100 can have 2, 3, or 4 channels 130 and each of the channels 130 can have a width ranging from 200 to 750 microns and a depth ranging from 10 to 1500 microns. The fluidics device 100 can include 2, 3, or 4 microchannels 200 that are contiguous with the channel 130 and each of the microchannels 200 can have a width ranging from 200 to 750 microns and a depth ranging from 10 to 1500 microns. An example of a fluidics device 100 having 3 microchannels 200 that are contiguous with the triangular-shape channel 130 is shown in FIG. 5.

The channel cover 230 can include 1 or more projections extending from the channel cover 230 such that when the channel cover 230 is engaged on top of the channels 130 of the fluidics device 100 the channel cover 230 defines 2 or more microchannels 200 contiguous with the channel 130. For example, the channel cover 230 can have two projections such that when the channel cover 230 is engaged on top of the channel 130 of the fluidics device 100 the channel cover 230 defines 3 microchannels 200 contiguous with the channel 130. In one embodiment, each of the microchannels 200 defined by the channel cover 230 can have a width ranging from 200 to 750 microns and a depth ranging from 10 to 1500 microns.

The bottom surface of each of the channels 130, the dosing well channel 150, the microchannels 200, and the collection well channels 210 can define different shapes. For example, the channels 130, the dosing well channel 150, the microchannels 200, and the collection well channels 210 can define an arcuate bottom surface or a generally flat bottom surface.

Figure 8:
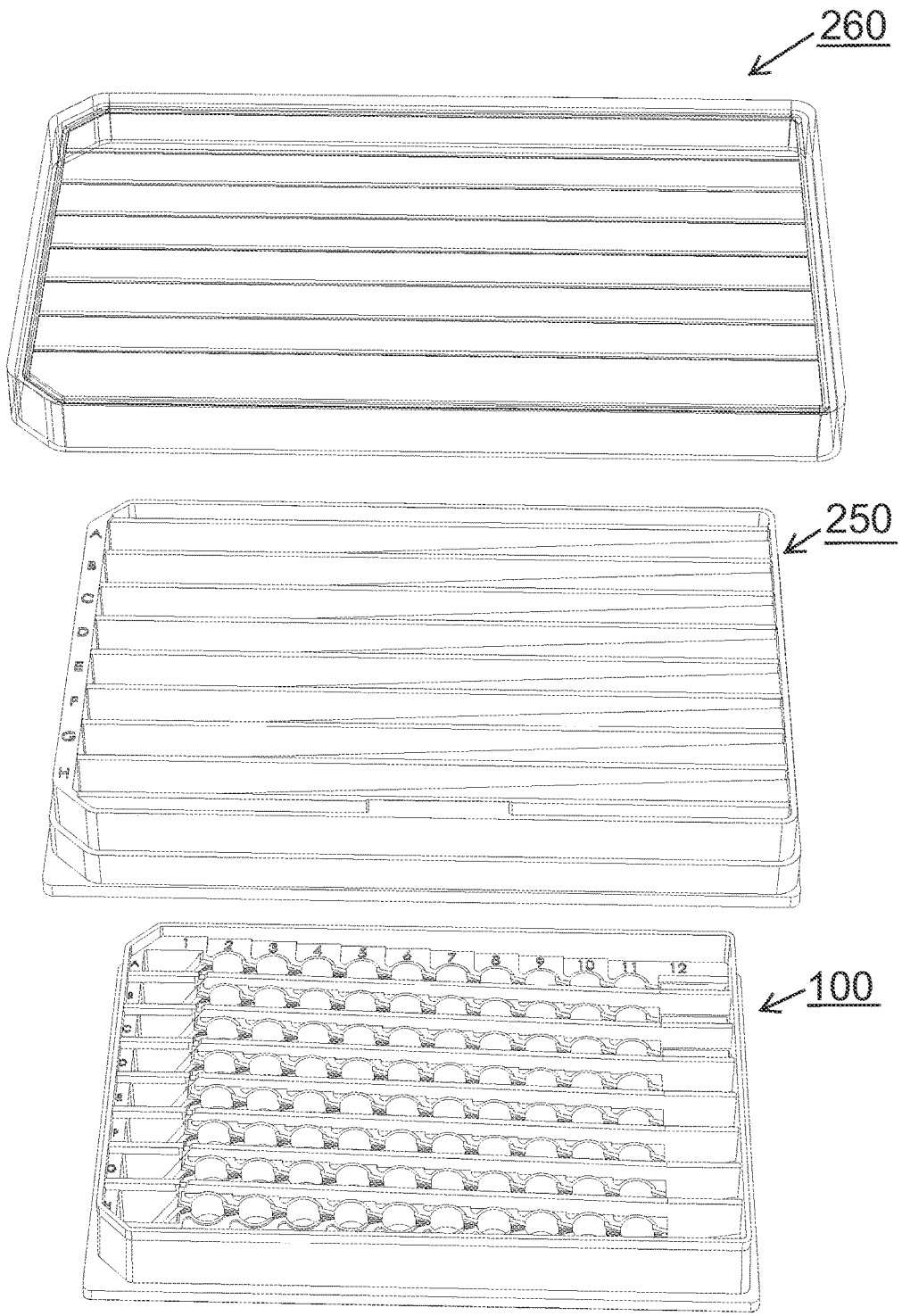
FIG. 8 shows an exploded perspective view of the fluidics device of FIG. 1 as part of an assembly including a reservoir tray nestably engaged on top of the fluidics device and a cover tray nestably engaged on top of the reservoir tray in accordance with embodiments of the present disclosure.

According to one or more embodiments, the fluidics device 100 can have a structure where the plurality of wells 120 are aligned in a row. The fluidics device 100 can have 12 wells in a respective row and a total of 8 rows. An example of a fluidics device 100 having this structure is shown in FIGS. 1, 2, and 8. The fluidics device 100 can have 3 wells in a row and a total of 2 rows. The fluidics device 100 can have 6 wells in a row and a total of 4 rows. The fluidics device 100 can have 8 wells in a row and a total of 6 rows. The fluidics device 100 can have 12 wells in a row and a total of 8 rows. The fluidics device 100 can have 24 wells in a row and a total of 16 rows. The fluidics device 100 can have 48 wells in a row and a total of 32 rows.

According to one or more embodiments, the fluidics device 100 can have a structure where the plurality of wells 120 for containing a respective host fluid are oriented in a configuration such that each downstream well 120 is positioned lower relative to each adjacent upstream well 120 and the dosing well 110 is upstream from the plurality of wells 120 and in fluid communication therewith.

The fluidics device 100 of the presently disclosed subject matter can be employed for any use requiring the tempered flow of fluid between a plurality of wells. According to one or more embodiments, a method for employing the fluidics device 100 includes adding a dosing fluid to the dosing well 110 and adding the respective host fluid to the plurality of wells 120 such that the fluid is in fluid contact with the channel fluid flow path 130, whereby the dosing fluid flows to each of the respective host fluids in the plurality of wells 120 in a tempered manner. The method can include removing an aliquot of the respective host fluid from the wells 120 at one or more time periods to measure the effect of the dosing fluid being tempered through the plurality of wells 120 over time.

The dosing fluid can include, for example, but is not limited to a drug, a legal or illegal drug, a toxin, an agent of warfare, a fragrance, a food spice, an oil, a gas, a metabolite, a compound, a hormone, a solution, a solute, a composite, a nutrient media, differentiation media, or a growth media, and combinations thereof. The plurality of wells 120 can contain a respective cell culture whereby an effect of the tempered exposure to the dosing fluid on the cells can be measured.

The effect of the tempered exposure to the dosing fluid on the cell cultures to be measured can be one or more of pharmacokinetics, drug metabolism, toxicity, pre-clinical pharmaceutical studies, cell response, cell receptor response, cell feedback signals, cell growth, cell death, cell differentiation, or cell regeneration, and combinations thereof. The respective cell culture can be, for example, a stem cell culture or a progenitor cell culture.

According to one or more embodiments, the plurality of wells 120 of the fluidics device 100 can contain a respective cell culture, and a method for employing the fluidics device 100 containing the respective cell cultures includes adding a dosing fluid to the dosing well 110, adding the desired respective host fluid to the wells 120 such that the fluid is in fluid contact with the channel fluid flow path 130. Subsequently, the dosing fluid flows to each of the respective host fluids in the plurality of wells 120 in a tempered manner. The method can further include removing an aliquot of the respective host fluid from the wells 120 at one or more time periods to measure the effect of the dosing fluid on the cells.

The fluidics device 100 can be made of any material that is suitable for use in fluid transfer between the plurality of wells 120. The type of material chosen can depend on the desired use of the fluidics device 100. For example, the user of the fluidics device 100 can choose the material based on the dosing well fluid that will be used and the expected interaction of the dosing well fluid with the material. Thus, the fluidics device 100 can be made of any suitable material including, for example, a polymer, a synthetic polymer, a TOPAS® COC polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, or a borosilicate, or combinations thereof. In addition, the dosing well channel cover 160, the channel cover 230, and the wick 140, 142, 144 may each be made from the same materials as the fluidics device 100. In one example, a user may wish to have each of the fluidics device 100, the dosing well channel cover 160, the channel cover 230, and the wick 140, 142, 144 made from the same material such that the interaction of the dosing well fluid with the material does not vary.

According to one or more embodiments, the surface of one or more of the plurality of wells 120 of the fluidics device 100 can be modified with one or both of a chemical layer or a protein layer to support a cell culture. The protein layer for supporting the cell cultures can include one or more of collagen I, collagen II, collagen III, laminin, or fibronectin, or combinations thereof.

Figure 6:
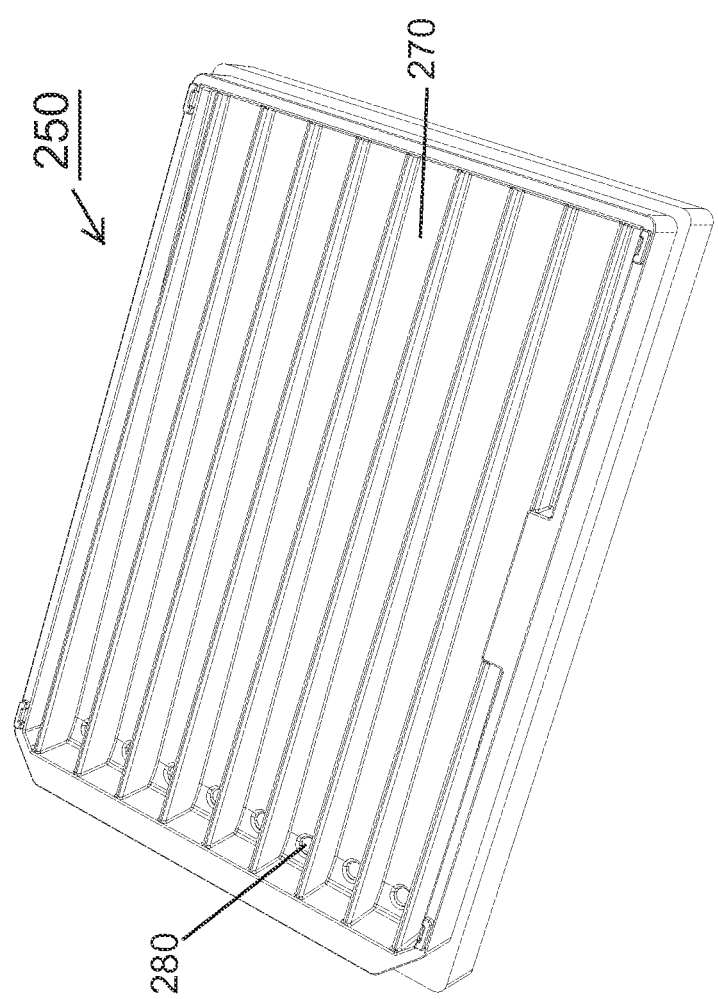
FIG. 6 shows a perspective view of the reservoir tray in accordance with embodiments of the present disclosure
Figure 7:
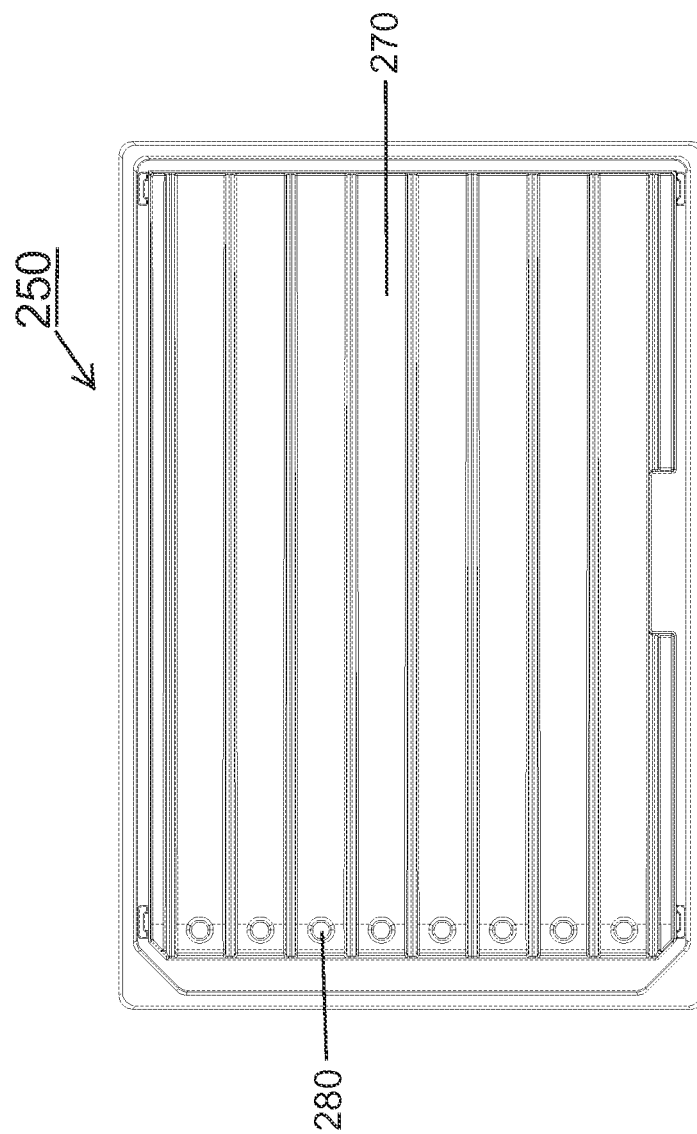
FIG. 7 shows a bottom view of the reservoir tray in accordance with embodiments of the present disclosure.

According to one or more embodiments of the presently disclosed subject matter, an assembly is provided for allowing fluid flow between the plurality of wells 120 of the fluidics device 100. The assembly can include the fluidics device 100 and a reservoir tray 250 configured for nesting engagement on top of the fluidics device 100. FIG. 6 shows a perspective view of the reservoir tray in accordance with embodiments of the present disclosure. FIG. 7 shows a bottom view of the reservoir tray in accordance with embodiments of the present disclosure. According to one or more embodiments, an assembly is provided that includes the fluidics device 100, the reservoir tray 250, and a cover tray 260 configured for nesting engagement on top of the reservoir tray 250 or the fluidics device 100. FIG. 8 shows an exploded perspective view of the fluidics device 100 as part of an assembly including the reservoir tray nestably engaged on top of the fluidics device 100 and the cover tray 260 nestably engaged on top of the reservoir tray in accordance with embodiments of the present disclosure.

According to one or more embodiments of the presently disclosed subject matter, an assembly is provided for allowing fluid flow between the plurality of wells 120 of the fluidics device 100, the assembly including the fluidics device 100 and the reservoir tray 250 configured for nesting engagement on top of the fluidics device 100. Turning to FIG.'s 6 and 7, the reservoir tray 250 can include at least one chamber 270 for containing a respective chamber fluid and an aperture 280 defined in the chamber floor and configured such that the aperture 280 is positioned above the dosing well 110 of the fluidics device 100 when in nesting engagement with the fluidics device 100. The floor of the chamber 270 can be angled and the aperture 280 can be defined at a lower portion of the chamber floor such that the chamber fluid flows through the aperture 280 into the dosing well 110 when the reservoir tray 250 and the fluidics device 100 are nestably engaged. When nestably engaged, the reservoir tray 250 can be positioned just above the fluidics device 100 and the respective chamber fluid flows from each chamber 270 of the reservoir tray 250 through each aperture 280 and into each dosing well 110 of the fluidics device 100.

According to one or more embodiments, the assembly can further include the cover tray 260 configured for nesting engagement on top of the reservoir tray 250 of the fluidics device 100. According to one or more embodiments, the assembly can include one or more additional reservoir trays 250 configured for nesting engagement on top of the fluidics device 100.

Figure 9:
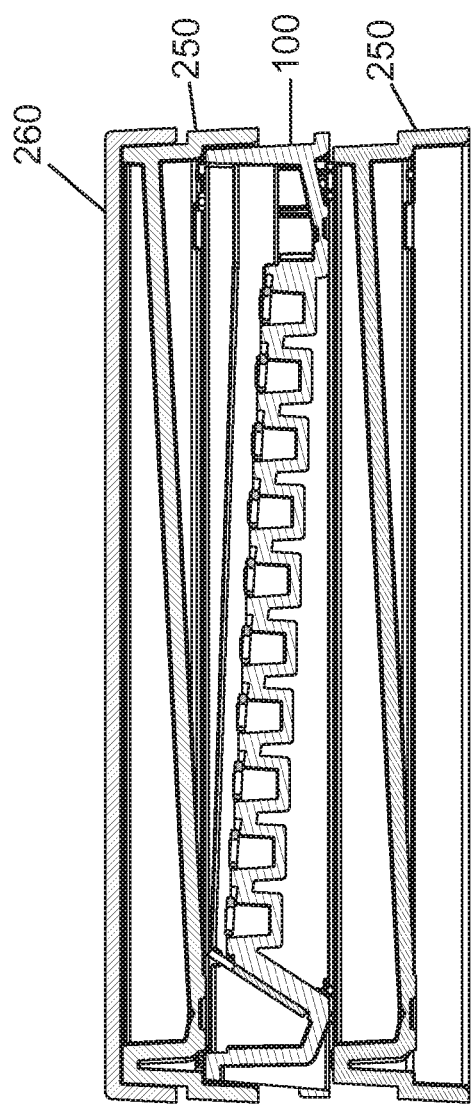
FIG. 9 shows a side view of the fluidics device of FIG. 1 as part of an assembly including a cover tray, a reservoir tray nestably engaged on top of the fluidics device, and a second reservoir tray nestably engaged underneath the fluidics device in accordance with embodiments of the present disclosure.

According to one or more embodiments of the presently disclosed subject matter, the assembly can further include a second reservoir tray 250 configured for nesting engagement underneath the fluidics device 100. FIG. 9 shows an exploded side view of this assembly including the second reservoir tray 250 in accordance with embodiments of the present disclosure. For this assembly, the fluidics device 100 can include the collection well 170 that is downstream from the plurality of wells 120 and the collection well 170 can define an aperture such that when the second reservoir tray 250 is in nesting engagement underneath the fluidics device 100, fluid from the collection well 170 of the fluidics device 100 flows through the aperture into the chamber 270 of the second reservoir tray 250. Referring to FIG. 9, the fluid can flow from the reservoir tray 250 nestably engaged on top of the fluidics device 100 from right to left through the aperture 280 of the reservoir tray 250 into the dosing well 110 of the fluidics device 100. The fluid can flow from the dosing well 110 from left to right through the aperture of the collection well 170 of the fluidics device 100 into the chamber 270 of the reservoir tray 250 nestably engaged underneath the fluidics device 100. The fluid can then flow in the second reservoir tray 250 from right to left.

According to one or more embodiments, the assembly can include one or more additional reservoir trays 250 configured for nesting engagement underneath the fluidics device 100.

According to one or more embodiments of the presently disclosed subject matter, the assembly can include a second fluidics device 100 configured for nesting engagement underneath the fluidics device 100. In this assembly, the fluidics device 100 can include the collection well 170 downstream from the plurality of wells 120 and the collection well 170 can define an aperture such that fluid from the collection well 170 flows through the aperture into the dosing well 110 of the second fluidics device 100 underneath when the fluidics devices 100 are nestably engaged.

Figure 10:
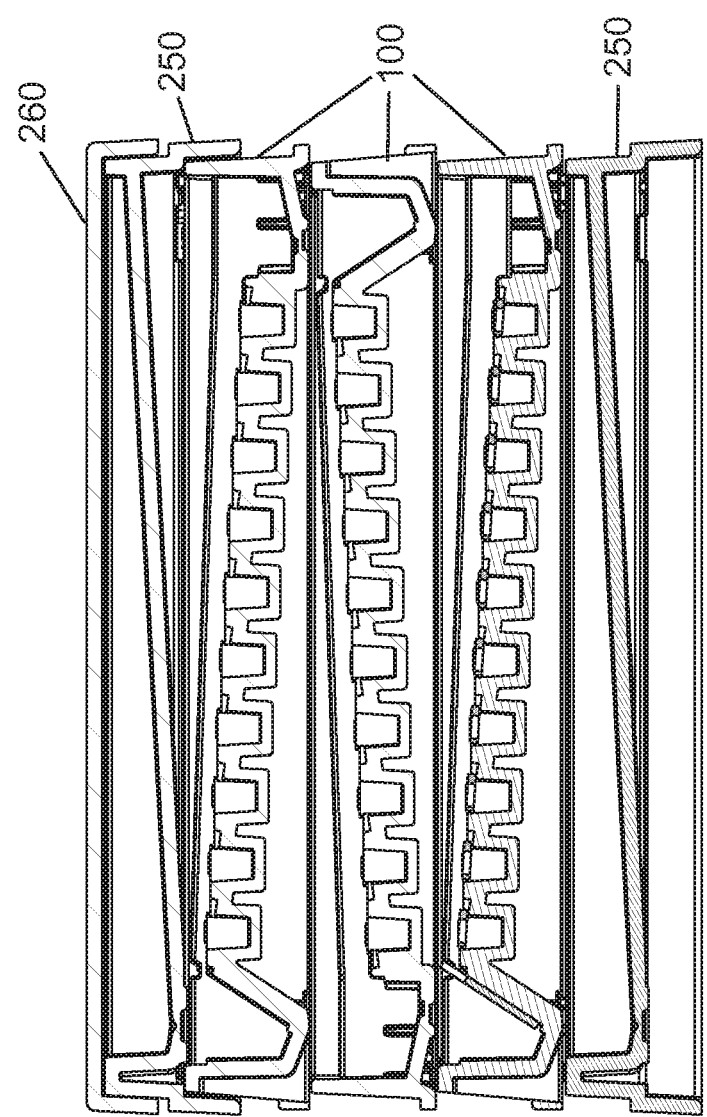
FIG. 10 shows a side view of the assembly of FIG. 9 further including two additional fluidics devices in nestable engagement in accordance with embodiments of the present disclosure.

According to one or more embodiments of the presently disclosed subject matter, the assembly can include one or more additional fluidics devices 100 configured for nesting engagement underneath the second fluidics device 100. The additional fluidics devices 100 can each include the collection well 170 downstream from the plurality of wells 120 and each collection well 170 can define an aperture such that fluid from the collection well 170 flows through the aperture into the dosing well 110 of the additional fluidics device 100 positioned underneath when the multiple fluidics devices 100 are nestably engaged. FIG. 10 shows an exploded side view of this assembly including a total of three fluidics devices 100 nestably engaged, reservoir trays 250 engaged on top of and underneath the three fluidics devices 100, and cover tray 260 engaged on top of the top reservoir tray 250 in accordance with embodiments of the present disclosure.

According to one or more embodiments of the presently disclosed subject matter, a method is provided for employing an assembly including one or more nestably engaged fluidics devices 100 and one or more reservoir trays 250 nestably engaged on top of and/or underneath the fluidics devices 100 as exemplified in FIGS. 8-10. The method can include adding a dosing fluid to the dosing well 120 and adding a respective host fluid to the plurality of wells 120 of the fluidics device(s) 100 such that the fluid is in fluid contact with the channel fluid flow path 130, whereby the dosing fluid flows to each of the respective host fluids in the plurality of wells 120 in a tempered manner. The method includes positioning the reservoir tray 250 above the fluidics device(s) 100 such that the reservoir tray 250 and the fluidics device(s) 100 are in nesting engagement, and adding the respective chamber fluid to the respective chamber 270 of the reservoir tray 250, whereby the respective chamber fluid flows into the dosing well 110 of the fluidics device 100 that is nestably engaged underneath the reservoir tray 250. In this manner, a larger supply of dosing fluid than can be contained by the dosing well 110 alone can be provided at a tempered rate to the one or more fluidics devices 100 that are nestably engaged underneath the reservoir tray 250.

According to one or more embodiments, the dosing fluid can include one or more of a drug, a legal or illegal drug, a toxin, an agent of warfare, a fragrance, a food spice, an oil, a gas, a metabolite, a compound, a hormone, a solution, a solute, a composite, a nutrient media, a differentiation media, or a growth media.

According to one or more embodiments, the plurality of wells 120 of the fluidics device 100 can contain a respective cell culture, whereby an effect of the tempered exposure to the dosing fluid on the cells can be measured. The effect of the tempered exposure to the dosing fluid on the cell cultures to be measured can be one or more of pharmacokinetics, drug metabolism, toxicity, pre-clinical pharmaceutical studies, cell response, cell receptor response, cell feedback signals, cell growth, cell death, cell differentiation, or cell regeneration. The respective cell culture can be a stem cell culture or a progenitor cell culture.

According to one or more embodiments, the method for employing the assembly can further include removing an aliquot of the respective host fluid from one or more of the plurality of wells 120 at one or more time periods to measure an effect of the dosing fluid from having been tempered through the plurality of wells 120. The plurality of wells 120 can contain a respective cell culture, and the method can include removing an aliquot of the respective host fluid from one or more of the plurality of wells 120 at one or more time periods to measure an effect of the dosing fluid on the cells.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A fluidics device comprising:
   a unitarily constructed tray configured to rest on a substantially flat surface including:
      a dosing well positioned upstream from a plurality of wells aligned in a row for containing a respective host fluid,
      wherein each of the plurality of wells defines a cavity having a bottom surface, a wall surface extending from the bottom surface and an open side defined by a circumference of the wall surface,
      wherein, when the tray rests on the flat surface, each of the open sides is in a step-down position relative to the open side of each adjacent upstream well and the wall surface is substantially perpendicular to the flat surface; and
      one or more channels extending between the open side of adjacent upstream wells and the open side of the adjacent downstream wells to define a channel fluid flow path there between.

2. The fluidics device of claim 1, further comprising a wick downstream from at least a portion of the plurality of wells and in fluid contact with the channel fluid flow path for regulating fluid flow through the plurality of wells.

3. The fluidics device of claim 2, wherein the device and/or the wick comprises one of a polymer, a synthetic polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, a borosilicate, and combinations thereof.

4. The fluidics device of claim 2, wherein the wick regulates fluid flow through the plurality of wells at a rate ranging from 0.0007 ml/min to 30 ml/min.

5. The fluidics device of claim 1, further comprising a collection well downstream from the plurality of wells to collect the respective host fluid after having flowed through the plurality of wells.

6. The fluidics device of claim 5, further comprising a wick contained in the collection well and the wick in fluid contact with the channel fluid flow path for regulating fluid flow through the plurality of wells.

7. The fluidics device of claim 6, wherein the wick is carried by a shoulder or by one or more posts defined by the collection well such that the wick does not contact a bottom surface of the collection well.

8. The fluidics device of claim 7, wherein the wick defines a gap such that only a portion of an edge of the wick is in fluid contact with the channel fluid flow path.

9. The fluidics device of claim 1, further comprising a dosing well channel extending from a bottom of the dosing well to the channel fluid flow path such that the dosing fluid flows to the respective host fluid of the adjacent downstream well through the dosing well channel and along the channel fluid flow path.

10. The fluidics device of claim 9, further comprising a dosing well channel cover configured to enclose the dosing well channel.

11. The fluidics device of claim 10, wherein the dosing well channel cover comprises one of a polymer, a synthetic polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, a borosilicate, and combinations thereof.

12. The fluidics device of claim 1, wherein a side of the dosing well defines an angle of greater than 90° extending from a bottom of the dosing well up to the channel fluid flow path of the adjacent well.

13. The fluidics device of claim 5, wherein the collection well has a floor defining a divot, wherein the floor is angled such that the divot is defined at a lower portion of the floor.

14. The fluidics device of claim 5, further comprising a collection well channel extending from the channel fluid flow path to a bottom of the collection well such that the respective host fluid of the adjacent upstream well flows along the channel fluid flow path and through the collection well channel into the collection well.

15. The fluidics device of claim 1, wherein the one or more channels has a width ranging from 10 to 3500 microns and a depth of 10 to 1500 microns.

16. The fluidics device of claim 1, wherein the one or more channels defines a triangular-shape extending between each of the adjacent wells and generally converging at each adjacent downstream well.

17. The fluidics device of claim 16, further comprising 2, 3, or 4 microchannels contiguous with the triangular-shape channel, and each of the microchannels having a width ranging from 200 to 750 microns and a depth of 10 to 1500 microns.

18. The fluidics device of claim 1, further comprising a channel cover configured for engagement on top of the one or more channels extending between the adjacent wells to enclose the channel.

19. The fluidics device of claim 18, wherein the channel cover comprises one of a polymer, a synthetic polymer, a biodegradable polymer, a plastic, a biodegradable plastic, a thermoplastic, a polystyrene, a polyethylene, a polypropylene, a polyvinyl chloride, a polytetrafluoroethylene, a silicone, a glass, a PYREX, a borosilicate, and combinations thereof.

20. The fluidics device of claim 1, comprising 12 wells in a respective row and a total of 8 rows.

21. The fluidics device of claim 1, wherein the plurality of wells contain a respective cell culture such that an effect on the cells of coming into contact with the dosing fluid can be measured.

22. The fluidics device of claim 21, wherein the respective cell culture is a stem cell culture or a progenitor cell culture.

23. The fluidics device of claim 1, wherein a surface of one or more of the plurality of wells is modified with one or both of a chemical layer and a protein layer to support a cell culture.

24. The fluidics device of claim 23, wherein the protein layer comprises one of collagen I, collagen II, collagen III, laminin, fibronection, and combinations thereof.

25. The fluidics device of claim 1, wherein the cavity of each of the downstream wells defines a substantially same volume and the bottom surface of each of the downstream wells defines a substantially same thickness.

26. The fluidics device of claim 1, wherein a dosing fluid deposited into the dosing well flows to the respective host fluid of the adjacent downstream well along the channel fluid flow path there between, and the respective host fluid subsequently flows to each adjacent downstream well along the channel fluid flow path there between.

27. An assembly for allowing fluid flow between a plurality of wells comprising:

a first fluidics device comprising:
  a dosing well positioned upstream from a plurality of wells aligned in a row for containing a respective host fluid,
  wherein each of the plurality of wells defines a cavity having a bottom surface a wall surface extending from the bottom surface and an open side defined by a circumference of the wall surface,
  wherein each of the open sides is in a step-down position relative to the open side of each adjacent upstream well; and
  one or more channels extending between the open side of adjacent upstream wells and the open side of the adjacent downstream wells to define a channel fluid flow path there between; and
a reservoir tray configured for nesting engagement on top of the first fluidics device, the reservoir tray comprising:
  at least one chamber for containing a respective chamber fluid; and
  a reservoir aperture defined in a floor of the at least one chamber and configured such that the reservoir aperture is positioned above the dosing well of the first fluidics device when in nesting engagement with the first fluidics device, wherein the floor of the at least one chamber is angled and the reservoir aperture is defined at a lower portion of the floor of the at least one chamber such that the chamber fluid flows through the reservoir aperture into the dosing well of the first fluidics device when the reservoir tray and the first fluidics device are nestably engaged.

28. The assembly of claim 27, further comprising a cover tray configured for nesting engagement on top of the reservoir tray or the first fluidics device.

29. The assembly of claim 27, wherein the first fluidics device comprises:
  a collection well downstream from the plurality of wells to collect the respective host fluid after its having flowed through the plurality of wells, wherein the collection well defines a collection aperture; and
  a second reservoir tray comprising at least one chamber for containing a respective chamber fluid and configured for nesting engagement underneath the first fluidics device such that fluid from the collection well of the first fluidics device flows through the collection aperture into the chamber of the second reservoir tray when the second reservoir tray and the first fluidics device are nestably engaged.

30. The assembly of claim 27, further comprising a second fluidics device configured for nesting engagement underneath the first fluidics device, wherein the first fluidics device comprises a collection well downstream from the plurality of wells to collect the respective host fluid after its having flowed through the plurality of wells, and wherein the collection well defines a collection aperture such that fluid from the collection well flows through the collection aperture into the dosing well of the second fluidics device when the first and second fluidics devices are nestably engaged.

31. The assembly of claim 30, further comprising one or more additional fluidics devices configured for nesting engagement underneath the second fluidics device, wherein the one or more additional fluidics devices each comprise an additional collection well downstream from a respective plurality of wells to collect the respective host fluid after its having flowed through the respective plurality of wells, and the additional collection well of each of the one or more additional fluidics device defines an additional aperture such that fluid from the additional collection well flows through the additional aperture into the dosing well of another one of the one or more additional fluidics device positioned underneath when the one or more additional fluidics devices are nestably engaged with the second fluidics device.

32. The fluidics device of claim 27, wherein the cavity of each of the downstream wells defines a substantially same volume and the bottom surface of each of the downstream wells defines a substantially same thickness.

33. The assembly of claim 27, wherein a dosing fluid deposited into the dosing well flows to the respective host fluid of the adjacent downstream well along the channel fluid flow path there between, and the respective host fluid subsequently flows to each adjacent downstream well along the channel fluid flow path there between.

\* \* \* \* \*